US007595102B2

United States Patent
Hill

(12) United States Patent
(10) Patent No.: US 7,595,102 B2
(45) Date of Patent: Sep. 29, 2009

(54) FINISHING POWDERS

(75) Inventor: David Michael Hill, Bishops Stortford (GB)

(73) Assignee: SSL International, Cambridge (GB)

( * ) Notice: Subject to any disclaimer, the term of this patent is extended or adjusted under 35 U.S.C. 154(b) by 480 days.

(21) Appl. No.: 10/522,634

(22) PCT Filed: Jul. 9, 2003

(86) PCT No.: PCT/GB03/02979

§ 371 (c)(1),
(2), (4) Date: Jan. 25, 2005

(87) PCT Pub. No.: WO2004/004797

PCT Pub. Date: Jan. 15, 2004

(65) Prior Publication Data

US 2006/0035040 A1 Feb. 16, 2006

(30) Foreign Application Priority Data

Jul. 9, 2002 (GB) .................. 0215905.1

(51) Int. Cl.
*B29D 22/00* (2006.01)
*B29D 23/00* (2006.01)
*B32B 1/08* (2006.01)
*B32B 27/32* (2006.01)

(52) U.S. Cl. .................. 428/35.2; 428/36.9; 428/36.91; 428/403; 428/407; 128/844

(58) Field of Classification Search ................ 428/403, 428/407, 36.2, 36.9, 36.91; 128/844
See application file for complete search history.

(56) References Cited

U.S. PATENT DOCUMENTS 4,143,423 A 3/1979 Sternlieb
5,405,666 A * 4/1995 Brindle ..................... 428/36.4
5,513,654 A * 5/1996 Delson ....................... 128/844

FOREIGN PATENT DOCUMENTS

WO WO94/15654 A1 7/1994

OTHER PUBLICATIONS

Odum, Brett C. et al., Influence of Absorbable Dusting Powders on Wound Infection, Journal of Emergency Medicine, vol. 16, No. 6, pp. 875-879, Elsevier Science, Inc. USA, 1998.
Kang, N. et al., The Pathological Effects of Glove and Condom Dusting Powders, Journal of Applied Toxicology, vol. 12(6), pp. 443-449, John Wiley & Sons, Ltd. UK, 1992.
World Health Organization; "The Male Latex Condom: Specification and Guidelines for Condom Procurement: (2003)"; Geneva, Switzerland.

* cited by examiner

*Primary Examiner*—Michael C Miggins
(74) *Attorney, Agent, or Firm*—Rankin, Hill & Clark LLP

(57) ABSTRACT

Substantially spherical water-insoluble inorganic particles are used as finishing powders for condoms.

23 Claims, 1 Drawing Sheet

Spherical basic magnesium carbonate

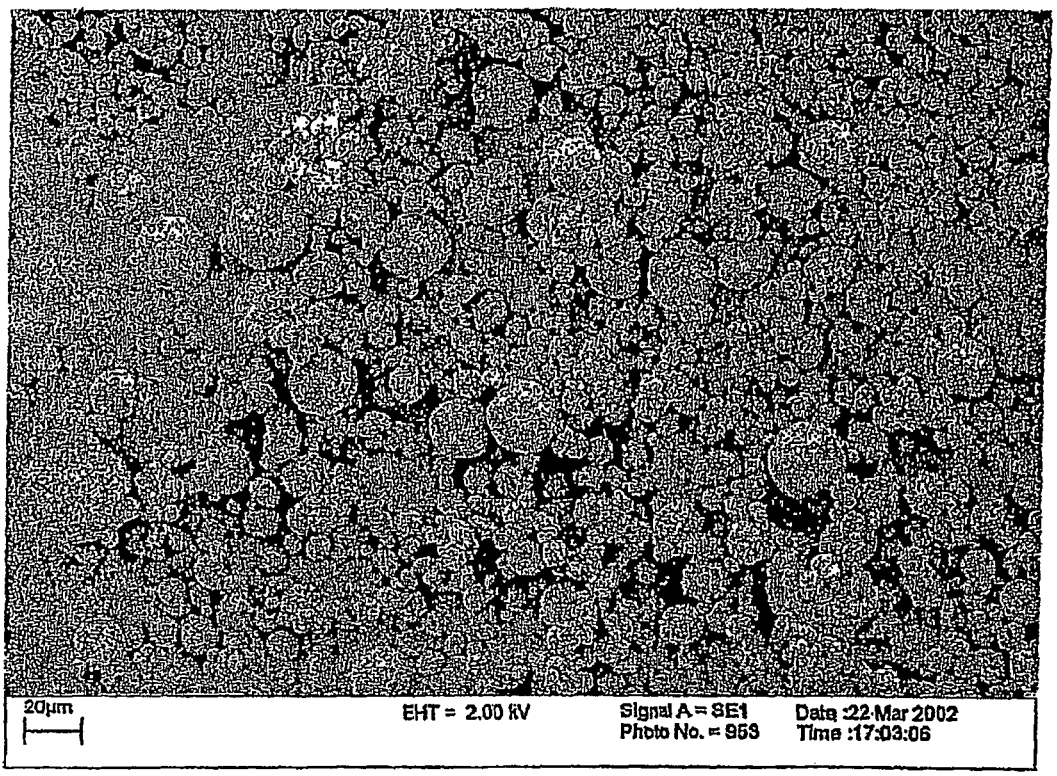
Figure 1: Spherical basic magnesium carbonate
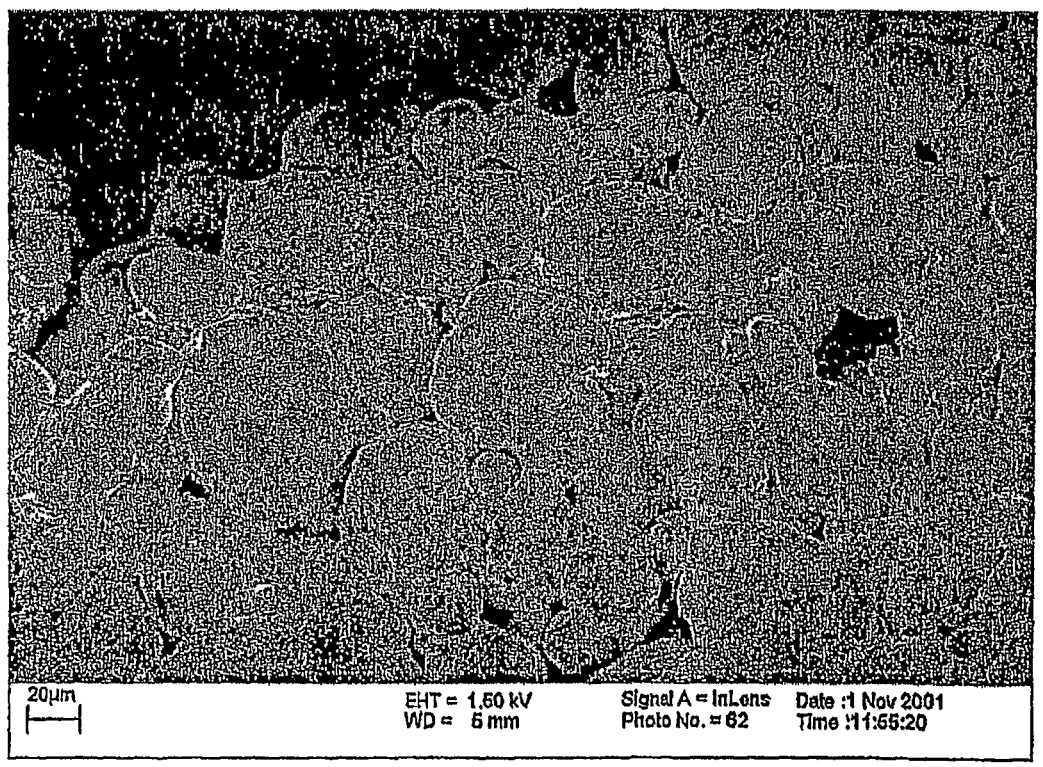
Figure 2: Standard basic magnesium carbonate

FINISHING POWDERS

BACKGROUND OF INVENTION

1. Field of Invention

This invention relates to finishing powders, particularly, but not exclusively, to finishing powders for condoms.

2. Description of Related Art

It is well known to use finishing powders in the man and production of both natal and synthetic rubber articles such as gloves and condoms. In the case of condoms, the finishing powder fulfills a number of functions, including the reduction of tack inherent on the untreated natural rubber surface and the provision of a low friction surface in order to facilitate transport of the condom on to mandrels and such like during automated processing. The finishing powder also enables a low friction surface to be maintained when the condom is in a rolled state to allow the condom to be handled easily by a foiling machine during packaging. Finally, in the case of condoms, the finishing powder allows the condom to be unrolled easily by the user.

A number of different finishing powders have been used for condoms in the past, including talc, mica, lycopodium and cross-linked maize starch. Owing to adverse clinical reports about mica, talc and lycopodium one of the most commonly used finishing powders now is cross-linked maize starch. This has many advantages as a finishing powder since it is available in a high state of purity, it is well tolerated by the body, it is bio-absorbable and it confers a low friction surface. However, more recently cross-linked maize starch has been shown to have a number of problems. For example, its bio-absorbable nature means that when used in aqueous slurries it is prone to microbial attack. To deal with this it is generally necessary to add biocides to the aqueous formulation, and these present a toxicity risk. There have also been reports that proteins present in, for example, natural rubber medical gloves can bind to cross-linked maize starch and thus possibly give an airborne route of exposure to the proteins, which are known to cause sensitisation problems in some users. (Refer, for example, to Beezhold, D. H. and Beck W. C. Archives of Surgery (1992), 127, 1354-1357.)

As a consequence of the above disadvantages, it has been recognised that there is a need to move away from starch to more advantageous finishing powders. One alternative has been to use inorganic powders such as calcium and magnesium carbonate. These compounds present advantages over cross-linked maize starch in that they have a good safety record, they are generally not susceptible to microbial spoilage and they do not bind the proteins found in natural rubber latex. On the whole, therefore, the industry has found it acceptable to use such compounds as satisfactory alternatives to starch.

However, we have found certain problems with inorganic carbonate finishing powders, which problems have hitherto not been recognised or appreciated. One problem is that the carbonates used up till now have been produced by standard manufacturing processes and these carbonates have an irregular or spicula particle morphology. As a consequence, they do not reduce friction anything like as well as starch. In particular, we have found that these standard carbonates, particularly magnesium carbonate, can give rise to problems during rolling and unrolling of a condom. Typically, when a condom is rolled off a shaped mandrel to give the familiar rolled condom, the rolling is applied from one side only. The action of rolling applies a localized strain to the side of the condom contacting the rolling belt or wheel, and if this strain is not dissipated within the condom, then one side of the condom can be more tightly rolled than the other. In addition, any misalignment (perhaps of only a few thousandths of an inch) can exacerbate this problem. Such a discrepancy of strain within the condom can give rise to difficulties when the user tries to unroll the condom. Cross-linked maize starch is very efficient at releasing these strains because of the low degree of friction it confers to the surfaces of the condom both during and after rolling. By contrast, however, we have found that when standard magnesium carbonate is used any differential stains created by the rolling are not released, but are retained within the rolled structure, giving rise to complaints of difficult unrolling by the condom user. Another problem we have discovered in using standard magnesium carbonate as a condom finishing powder is that the powder can impede migration of condom lubricant within the rolled condom structure. Typically lubricant is applied to a rolled condom just before packaging and it migrates along the rolled condom film whilst inside the foil pack. The inhibition of migration of lubricant appears to arise because of affinity between standard magnesium carbonate and the lubricant typically used for condoms. The lubricant appears to become "bound" to the standard magnesium carbonate, forming a stiff paste which effectively seals off the remainder of the condom body, preventing the rest of the lubricant from migrating down the condom body. We have found that 1 g of standard magnesium carbonate can bind up to 4.4 g of lubricant. The resulting absence of lubricant towards the closed end of the condom can again add to the difficulty in unrolling the condom, and generate user complaints about "dry" condoms.

BRIEF SUMMARY OF THE INVENTION

Having appreciated the above problems, we have now found a way of overcoming or substantially reducing them.

According to one aspect of the present invention, there is provided the use of a particulate, substantially water-insoluble, inorganic compound having substantially spherical particle morphology as a condom finishing powder.

The invention also includes a condom having thereon a finishing powder which is a particulate, substantially water-insoluble, inorganic compound having substantially spherical particle morphology.

By substantially spherical we mean particles having a circularity factor (c.f.) (as defined herein) less than that of standard grade magnesium carbonate. Preferably, the c.f. value is 15 or below. More preferably, the c.f. value is 14 or below.

By substantially water-insoluble we mean a compound having a solubility of less than about 0.05 g per 100 g of water. For example, magnesium carbonate has a solubility of 0.03-0.04 g/100 g cold water, while calcium carbonate has a solubility of 0.0015-0.002 g/100 g water. Suitably spherical forms of either of these materials can, for example, be employed.

In another aspect, the invention provides the use of spray dried magnesium carbonate as a condom finishing powder and includes a condom having thereon a finishing powder which is spray dried magnesium carbonate.

BRIEF DESCRIPTION OF THE DRAWINGS

FIG. 1 is a photomicrograph of particles of spray dried magnesium carbonate.

FIG. 2 is a photomicrograph of particles of standard magnesium carbonate made according to the Pattison process.

DETAILED DESCRIPTION OF THE INVENTION

We have found that the use of a substantially water-insoluble inorganic compound having substantially spherical particle morphology, as a condom finishing powder substantially eliminates the disadvantages associated with starch and standard inorganic carbonate powders whilst retaining the advantageous qualities of each. Preferably, the compound is a salt. It is particularly preferred to use magnesium carbonate having substantially spherical particle morphology (hereinafter referred to as "spherical magnesium caroonate"). An especially preferred form of this material is "spherical basic magnesium carbonate", which is a mixture of magnesium carbonate and hydrated magnesium hydroxide. This compound can be described approximately by the formula $5MgO.4CO_2.5H_2O$ or $(MgCO_3)_4Mg(OH)_2.4H_2O$. We have found that these compounds give excellent results even when a condom is rolled from one side only. The unrolling of such condoms by the user is easier than with standard magnesium carbonate, and they do not impede the migration of lubricant within the rolled condom Thus, in a her aspect, the invention provides a process for rolling a condom with finishing powder thereon from an unrolled state to a rolled state or vice versa which process comprises rolling the condom by applying suitable rolling means to one side of the condom only, characterised in that the said finishing powder is a substantially water-insoluble, inorganic compound having substantially spherical particle morphology.

We prefer to use magnesium carbonate which has been spray dried, since good particle sphericity is obtained in this way. However, other suitable methods of manufacture can be used provided that the end result ensures that a substantial number of the particles are of a broadly spherical nature. One suitable process for producing spray-dried, spherical material is the Aman process (refer, for example, to http://www.periclase.com for further details), which converts a concentrated magnesium chloride brine to magnesium carbonate via thermal decomposition of the brine in a spray roaster. One particularly preferred product is heavy CP14 $MgCO_3$ which is a spray dried product (as supplied, for example, in pharmaceutical quality, by Lehvoss, UK). This product is equivalent to "spherical basic magnesium carbonate" (see above), particles of which are shown in the photomicrograph of FIG. 1. The sphericity of the particles gives a powder having excellent low friction properties.

By "standard magnesium carbonate" we mean pharmaceutical grade light magnesium carbonate. This material is normally produced by the Pattison process (refer, for example, to British patent specification no. 9102 to H. L. Pattison), which converts dolomite (a mixed magnesium/calcium carbonate) into calcium carbonate and either magnesium oxide or magnesium carbonate. Other processes, as will be clear to those skilled in the art, are, however, also used in the manufacture of standard magnesium carbonate. A photomicrograph of particles of standard magnesium carbonate made according to the Pattison process is shown in FIG. 2. It can readily be seen that this material does not possess good sphericity. Similar results are obtained with material made according to other conventionally used processes for making pharmaceutical grade light magnesium carbonate.

There are various approaches to measuring sphericity or degree of roundness. One is based upon:

$$\text{Circularity factor } (c.f.) = \frac{p^2}{A}$$

where p=perimeter of 2-D image of particle
A=projected area (i.e. area of 2-D image of particle)

This definition (as with others) is based upon 2-D projections or images of 3-D particles (as viewed under a microscope, for example) and hence is relatively easy to calculate. A perfect sphere has a circularity factor of 4Π or 12.57. Obviously, for non-perfect 3-D particles a number of measurements will have to be made to generate an average. This can be done with a reasonable degree of accuracy using images of particles in micrographs, or using images as viewed directly with a microscope.

We prefer to use particles whose circularity factor (as measured in the above way) approaches, or comes close to, that of a perfect sphere. For standard magnesium carbonate (made according to the Pattison process, and which gives inferior performance), we have obtained a c.f. value of 16.7. Better performance is achieved with particles having a value less than this, and so we prefer to use such particles. For example, our preferred spherical basic magnesium carbonate (CP14, above) has been found to have a c.f. value of about 13.6.

In terms of particle size distribution, our preferred spherical basic magnesium carbonate powder (CP14, above) contrasts with standard (or light grade) magnesium carbonate as follows:

| Powder | Lower 10% | Median | Upper 90% |
|---|---|---|---|
| Spherical basic $MgCO_3$ | 4 μm | 11 μm | 26 μm |
| | 3 μm | 10 μm | 21 μm |
| Light grade $MgCO_3$ | 2 μm | 8 μm | 26 μm |

The above data show the proportion of particles [volume %] in terms of the diameter below which 10% of the particles lie, the median value, and the value below which 90% of the particles lie. The data for the spherical grade show fewer smaller particles than the light grade.

The finishing powders employed in the present invention can be used in the normal way, as will be well understood by those skilled in the art. Thus, in general, a condom-shaped former will be dipped in, for example, natural rubber latex so as to create a rubber film on the former. After drying, the condom is stripped off the former and washed in an aqueous dispersion of the finishing powder. After drying, the condom is transferred to the electronic testing mandrel. The condom is then rolled up the mandrel in order to produce a rolled condom by applying rolling means, typically a rolling belt, to one side of the condom. The rolled condom is then removed and packaged together with lubricant in the usual way.

Whilst the present finishing powders are particularly suitable for use in a process in which the condom is rolled up a mandrel on one side only, they can also be used with excellent results in condom rolling processes generally, owing to their advantages over the finishing powders used heretofore.

The present finishing powders can also be mixed with known finishing powders—for example, a mixture of spherical or spherical basic magnesium carbonate with calcium carbonate, provided that the advantages afforded by the powders of the invention are not diminished to any significant degree. When such mixtures are used, we prefer the powder of the invention to be present in an amount of at least 40% by weight of the total powder composition.

In order that the invention may be more fully understood, the following Examples are given by way of illustration only.

Example 1

The ease of unrolling, and the lubricant migration, were tested in rolled condoms according to the invention and in rolled control condoms. The condoms of the invention had been made using spherical magnesium carbonate finishing powder in accordance with the invention, and the control condoms were made using light magnesium carbonate finishing powder, i.e. standard magnesium carbonate of normal particle morphology, and calcium carbonate. The following results were obtained:

| Parameter | New Condom Finish | Control |
| --- | --- | --- |
| Initial subjective unrolling | Grade 1* | Grade 1.2* |
| Aged (7 days/70°) subjective unrolling | Grade 1.1* | Grade 2.6* |
| Initial timed unrolling | 1.1 seconds | 1.4 seconds |
| Aged (7 days/70°) timed unrolling | 2.2 seconds | 5.3 seconds |
| Initial lubricant migration | 74 mm | 27 mm |
| Aged (7 days/70°) lubricant migration | 91 mm | 45 mm |

*mean of 5 or 10 replicates Physical properties were good for both condom types.

Physical properties were good for both condom types.

Subjective unrolling grades the ease of unrolling in the following categories:

| | |
| --- | --- |
| Grade 1 | Very easy |
| Grade 2 | Easy |
| Grade 3 | Moderate |
| Grade 4 | Difficult |
| Grade 5 | Cannot be unrolled. |

Timed unrolling is the meantime for the condom to unroll when a weight is attached to the teat whilst the rest of the condom body is supported.

The formulations used in this work were:

| | New Finish | Control |
| --- | --- | --- |
| Spherical magnesium carbonate | 2.0% | — |
| Light mag. carb (i.e. normal particle morphology) | — | 2.0% |
| Calcium carbonate | — | 0.5% |
| Silicone emulsion | 0.5% | 0.51% |
| Biocide | 0.1% | 0.1% |
| Surfactant | 0% | 0.025% |
| Water | 97.4% | 96.865% |

Example 2

Similar tests to Example 1 were carried out with other condoms, one in accordance with the invention, and the other as controls. The results were:

| Parameter | New Condom Finish | Control |
| --- | --- | --- |
| Initial subjective unrolling | Grade 1* | Grade 2* |
| Subjective unrolling after maturation | Grade 1.5* | Grade 2.5* |
| Initial timed unrolling | 1.2 seconds | 1.4 seconds |
| Timed unrolling after maturation | 1.4 seconds | 2.6 seconds |
| Initial lubricant migration | 130 mm | 62 mm |
| Lubricant migration after maturation | 132 mm | 57 mm |

*mean of 5 or 10 replicates Physical properties were good for both condom types.

Physical properties were good for both condom types. The formulations used in his work were:

| | New Finish | Control |
| --- | --- | --- |
| Spherical magnesium carbonate | 2.5% | — |
| Light mag. carb (i.e. normal particle morphology) | — | 2.0% |
| Calcium carbonate | — | 0.5% |
| Silicone emulsion | 0.5% | 0.51% |
| Biocide | 0.1% | 0.1% |
| Surfactant | 0.025% | 0.025% |
| Water | 96.875% | 96.865% |

The results showed a clear preference for the new finish.

The invention claimed is:

1. A condom comprising a finishing powder which comprises a particulate, substantially water-insoluble, inorganic compound having substantially spherical particle morphology, wherein the inorganic compound is a salt, and wherein the salt is basic magnesium carbonate which is a mixture of magnesium carbonate and hydrated magnesium hydroxide.

2. A condom comprising a finishing powder which comprises a particulate, substantially water-insoluble, inorganic compound having an average circularity factor of 15 or below, wherein the circularity factor for each particle used to generate the average is measured according to the formula:

$$\text{circularity factor} = p^2/A$$

where p is the perimeter of a 2-D image of the particle and A is the area of the 2-D image of the particle.

3. A condom according to claim 2 wherein the average circularity factor is 14 or below.

4. A condom according to claim 2 wherein the inorganic compound has a water solubility of less that 0.05 g per 100 g of water.

5. A condom according to claim 2 wherein the inorganic compound is a salt.

6. The condom according to claim 5 wherein the salt is magnesium carbonate or calcium carbonate.

7. A condom according to claim 2 wherein the inorganic compound has been spray dried.

8. A condom according to claim 7 wherein the inorganic compound is spray dried magnesium carbonate.

9. A condom according to claim 7 wherein the inorganic compound has been made according to the Aman process.

10. A condom according to claim 7 wherein the inorganic compound has a water solubility of less that 0.05 g per 100 g of water.

11. A condom according to claim 7 wherein the inorganic compound is a salt.

12. The condom according to claim 11 wherein the salt is magnesium carbonate or calcium carbonate.

13. A condom comprising a finishing powder which comprises a particulate, substantially water-insoluble, inorganic compound having an average circularity factor of 15 or below, wherein the circularity factor for each particle used to generate the average is measured according to the formula:

$$\text{circularity factor} = p^2/A$$

where p is the perimeter of a 2-D image of the particle and A is the area of the 2-D image of the particle and wherein the particles are non-immobilized on the surface of the condom.

14. A condom according to claim 13 wherein the average circularity factor is 14 or below.

15. A condom according to claim 13 wherein the inorganic compound has a water solubility of less that 0.05 g per 100 g of water.

16. A condom according to claim 13 wherein the inorganic compound is a salt.

17. The condom according to claim 16 wherein the salt is magnesium carbonate or calcium carbonate.

18. A condom according to claim 13 wherein the inorganic compound has been spray dried.

19. A condom according to claim 18 wherein the inorganic compound is spray dried magnesium carbonate.

20. A condom according to claim 18 wherein the inorganic compound has been made according to the Aman process.

21. A condom according to claim 18 wherein the inorganic compound has a water solubility of less that 0.05 g per 100 g of water.

22. A condom according to claim 18 wherein the inorganic compound is a salt.

23. The condom according to claim 22 wherein the salt is magnesium carbonate or calcium carbonate.

* * * * *